(12) United States Patent
Zhu et al.

(10) Patent No.: US 11,340,117 B2
(45) Date of Patent: May 24, 2022

(54) METHOD AND DEVICE FOR MEASURING BODY TEMPERATURE AND SMART APPARATUS

(71) Applicant: Goertek Inc., Weifang (CN)

(72) Inventors: Jian Zhu, Weifang (CN); Xiangdong Zhang, Weifang (CN); Zhenyu Yu, Weifang (CN); Zhiping Luo, Weifang (CN); Dong Yan, Weifang (CN)

(73) Assignee: GOERTEK INC., Weifang (CN)

( * ) Notice: Subject to any disclaimer, the term of this patent is extended or adjusted under 35 U.S.C. 154(b) by 666 days.

(21) Appl. No.: 16/097,718

(22) PCT Filed: May 24, 2018

(86) PCT No.: PCT/CN2018/088198
§ 371 (c)(1),
(2) Date: Oct. 30, 2018

(87) PCT Pub. No.: WO2019/015390
PCT Pub. Date: Jan. 24, 2019

(65) Prior Publication Data
US 2020/0256734 A1 Aug. 13, 2020

(30) Foreign Application Priority Data
Jul. 20, 2017 (CN) .......................... 201710597817.5

(51) Int. Cl.
*G01J 5/00* (2022.01)
*A61B 5/01* (2006.01)
(Continued)

(52) U.S. Cl.
CPC ............ *G01J 5/0025* (2013.01); *A61B 5/015* (2013.01); *A61B 5/6887* (2013.01); *G01J 5/0806* (2013.01); *G01S 15/08* (2013.01)

(58) Field of Classification Search
CPC .......................... A61B 5/01; A61B 2562/0257
(Continued)

(56) References Cited

U.S. PATENT DOCUMENTS

2015/0150453 A1* 6/2015 Abreu .................. A61B 5/0075
600/474
2016/0113517 A1* 4/2016 Lee ....................... H04N 5/2171
600/474

(Continued)

FOREIGN PATENT DOCUMENTS

CN 202515650 U 11/2012
CN 204698531 U 10/2015
(Continued)

*Primary Examiner* — Fabricio R Murillo Garcia
(74) *Attorney, Agent, or Firm* — Fox Rothschild LLP; Carol E. Thorstad-Forsyth

(57) ABSTRACT

A method and device for measuring body temperature and a smart apparatus are disclosed. The method comprises: when a temperature measuring instruction is received, starting a camera and a first infrared thermometer; photographing a user by using the camera to obtain an image, and identifying the image to determine a part to be measured of the user; acquiring a distance between the first infrared thermometer and the user; when the distance is equal to a preset distance threshold, controlling the first infrared thermometer to measure the temperature of the part to be measured of the user; wherein the preset distance threshold is set according to a focal length of a Fresnel lens of the first infrared thermometer; and according to a preset rule and the measured temperature, determining a value or a value range of the user's body temperature.

17 Claims, 4 Drawing Sheets

(51) Int. Cl.
*A61B 5/00* (2006.01)
*G01J 5/0806* (2022.01)
*G01S 15/08* (2006.01)

(58) Field of Classification Search
USPC .......................................................... 374/129
See application file for complete search history.

(56) References Cited

U.S. PATENT DOCUMENTS

2017/0065183 A1* 3/2017 Abreu .................. A61B 5/6803
2017/0095205 A1* 4/2017 Abreu .................. A61B 5/6833

FOREIGN PATENT DOCUMENTS

| | | |
|---|---|---|
| CN | 105125181 A | 12/2015 |
| CN | 107019498 A | 8/2017 |
| CN | 107361748 A | 11/2017 |
| DE | 202011051072 U1 | 10/2011 |

* cited by examiner

METHOD AND DEVICE FOR MEASURING BODY TEMPERATURE AND SMART APPARATUS

CROSS REFERENCE TO RELATED APPLICATIONS

This application is a U.S. National Stage entry under 35 U.S.C. § 371 based on International Application No. PCT/CN2018/088198, filed on May 24, 2018, which was published under PCT Article 21(2) and which claims priority to Chinese Patent Application No. 201710597817.5, filed on Jul. 20, 2017. The disclosure of the priority applications are hereby incorporated herein in their entirety by reference.

TECHNICAL FIELD

The present disclosure relates to a method and device for measuring body temperature and a smart apparatus.

BACKGROUND

The most common body temperature thermometer is the contact thermometer, which is used to measure the armpit temperature or mouth temperature of the user. However, the objects to be measured by the contact thermometer are limited; for example, it is inconvenient to measure a child's temperature. In the prior art there is a non-contact infrared thermometer, which can measure the forehead temperature or ear temperature of the user. However, currently the working distance of non-contact infrared thermometers is only about 3 cm, which cannot satisfy the requirement of long-distance temperature measurement.

SUMMARY

The present disclosure provides a method and device for measuring body temperature and a smart apparatus, to satisfy the requirement of long-distance temperature measurement, and improve the accuracy of body temperature measurement.

According to an aspect of the present disclosure, there is provided a method for measuring body temperature, comprising:

starting a camera and a first infrared thermometer when a temperature measuring instruction is received;

photographing a user by using the camera to obtain an image, and identifying the image to determine a part to be measured of the user;

acquiring a distance between the first infrared thermometer and the user;

controlling the first infrared thermometer to measure the temperature of the part to be measured of the user when the distance is equal to a preset distance threshold, wherein the preset distance threshold is set according to a focal length of a Fresnel lens of the first infrared thermometer; and determining a value or a value range of the user's body temperature according to a preset rule and the measured temperature.

According to another aspect of the present disclosure, there is provided a device for measuring body temperature, comprising: a main body, a microprocessor provided on the main body, and a camera and a first infrared thermometer that are connected to the microprocessor;

wherein the microprocessor, when a temperature measuring instruction is received, starts the camera and the first infrared thermometer;

after being started, the camera photographs a user to obtain an image, and sends the image to the microprocessor; and the microprocessor determines a part to be measured of the user according to the received image, and according to an acquired distance between the first infrared thermometer and the user, when it is determined that the distance is equal to a preset distance threshold, controls the first infrared thermometer to measure a temperature of the part to be measured of the user, and processes the temperature to obtain a value or a value range of the user's body temperature;

wherein the preset distance threshold is set according to a focal length of a Fresnel lens of the first infrared thermometer.

According to yet another aspect of the present disclosure, there is provided a smart apparatus, comprising a machine-readable storage medium and a processor that are communicatively connected by an internal bus, wherein the machine-readable storage medium stores a computer program executable by the processor, and when executed by the processor the computer program implements the steps of the method for measuring body temperature of an aspect of the present disclosure.

The advantageous effects of the present disclosure are as follows. The body temperature measurement solutions of the embodiment of the present disclosure, by identifying the image obtained by photographing the user to determine the part to be measured of the user, judging the distance between the user and the first infrared thermometer, and when the distance is equal to a preset distance threshold, controlling the first infrared thermometer to measure the temperature of the part to be measured, realize long-distance body temperature measurement without limitation on the objects to be measured. Furthermore, the preset distance threshold is set according to the focal length of the Fresnel lens of the first infrared thermometer; that is, only when the user is at a position adjacent to the focal length, the body temperature measurement is conducted, which improves the accuracy and the reliability of the body temperature measurement result. The present disclosure determines the part to be measured by referring to the identifying of the image photographed by the camera, measures the temperature of the part to be measured, and according to the preset rule and the temperature of the part to be measured, converts the temperature of the part to be measured into the body temperature value of the user, which reduces the temperature measurement error between different parts of human body, and further improves the accuracy of the measured body temperature of the user.

BRIEF DESCRIPTION OF DRAWINGS

In order to more clearly illustrate the technical solutions of the present disclosure or the prior art, the drawings used in the embodiments will be briefly described below. Apparently, the drawings described below are merely examples of the present disclosure, and a person skilled in the art can obtain other drawings according to these drawings without paying creative work.

DETAILED DESCRIPTION

Figure 1:
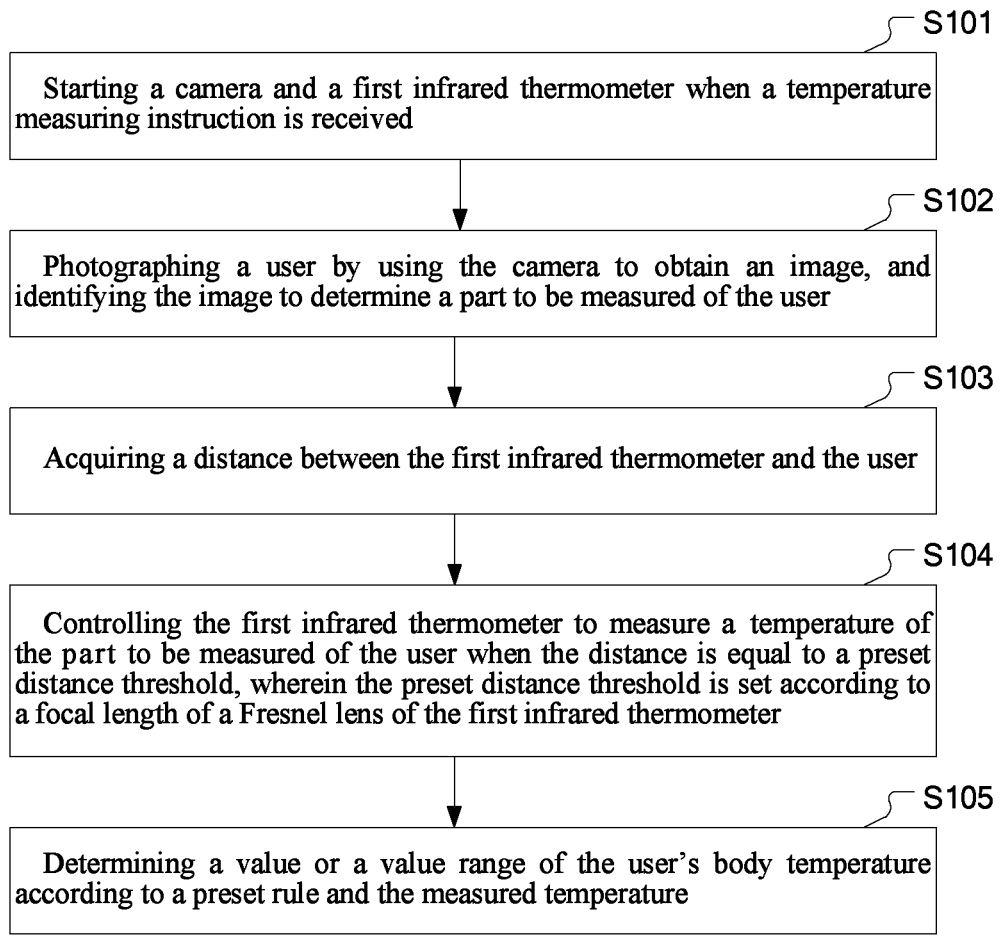
FIG. 1 is a schematic flow diagram of a method for measuring body temperature according to an embodiment of the present disclosure.

Currently the most common body temperature thermometer is the contact thermometer, although non-contact infrared thermometers are also available. The inventors of the present application found that when non-contact infrared body temperature thermometers are used for long-distance (for example, a distance of over 20 cm) measurement the accuracy usually cannot be guaranteed. Experiments have shown that the measuring error of non-contact infrared body temperature thermometers is typically greater than 1 degree Celsius. If a body temperature of 38 degree Celsius of a child having a fever is improperly measured as a normal body temperature of 37 degree Celsius, such a measurement result is not only invalid but also dangerous.

At present, the factors that affect the accuracy of infrared body temperature measurement mainly include:

(1) In long-distance body temperature measurement, both the infrared sensor and a Fresnel lens are needed to acquire the infrared light intensity of a remote object to realize body temperature measurement. Since the focal point of the Fresnel lens is fixed, only the measurement result of an object near the focal point of the Fresnel lens is reliable. For example, when a Fresnel lens with a focal length of 50 cm is selected, the temperature of a point at a part to be measured (for example, the forehead) of the user can be measured at a position corresponding to the focal point at a distance of 50 cm. If the user is deviated from the focal point, the infrared sensor will measure the average temperature of an area of the forehead. The farther the user is away from the focal point, the larger the measured area is (for example, even larger than the area of the whole forehead), and the more inaccurate of measurement result is.

(2) As different objects have different infrared emissivity, the infrared energies they radiate are also different even if their temperature is the same. For example, the infrared energies radiated by a human body skin of 37 degree Celsius and a wall of 37 degree Celsius are greatly different. Therefore, the difference between the temperature of the part to be measured and the body temperature must be considered, to obtain an accurate value of body temperature.

(3) The transmission of infrared energy is also greatly related to actual environmental factors (such as temperature, humidity and dust concentration of the environment). The longer the measurement distance is, the greater the influence of the environment is, and the worse the accuracy of measurement result is. In long-distance measurement, how to ensure the measurement accuracy is an urgent problem to solve.

Considering the above factors affecting the accuracy of infrared body temperature measurement and the technical problems, the present disclosure provides a method for measuring body temperature to improve the measurement accuracy of infrared body temperature measurement and realize long-distance non-contact body temperature measurement.

It should be noted that, the embodiments described below are merely some rather than all embodiments of the present disclosure. All other embodiments that are obtained on the basis of the embodiments of the present disclosure by a person skilled in the art without paying creative work shall fall within the protection scope of the present disclosure.

Referring to FIG. 1, the method for measuring body temperature of the present embodiment comprises the following steps:

Step S101, starting a camera and a first infrared thermometer when a temperature measuring instruction is received;

Step S102, photographing a user by using the camera to obtain an image, and identifying the image to determine a part to be measured of the user;

Step S103, acquiring a distance between the first infrared thermometer and the user; Step S104, controlling the first infrared thermometer to measure a temperature of the part to be measured of the user when the distance is equal to a preset distance threshold, wherein the preset distance threshold is set according to a focal length of a Fresnel lens of the first infrared thermometer; and Step S105, determining a value or a value range of the user's body temperature according to a preset rule and the measured temperature.

As can be seen from FIG. 1, in the method for measuring body temperature of the present embodiment, the user is photographed by a camera to obtain an image, and the image is identified to determine the part to be measured. It is judged according to the acquired distance between the first infrared thermometer and the user whether the distance is equal to a preset distance threshold, and if yes, the first infrared thermometer is controlled to measure the temperature of the part to be measured of the user, thereby realizing long-distance body temperature measurement in which the objects to be measured are not limited. Moreover, the part to be measured of the user is measured at the position where the distance between the first infrared thermometer and the user is equal to the focal length of the Fresnel lens, which ensures the infrared measurement distance, avoids the measurement error caused by the deviation of the center line of the infrared thermometer from the focal point of the Fresnel lens in infrared measurement, and improves the accuracy of the measurement result. Further, regarding the influence of the factor that different parts of the human body have temperature differences, in the present embodiment, after the temperature value of the part to be measured of the user is obtained, it is not directly used as the body temperature value of the user, but is converted into the body temperature value of the user according to the preset rule, to ensure that a more accurate body temperature value can be obtained.

A feasible way of acquiring the distance between the first infrared thermometer and the user in Step S103 is using a distance sensor (for example, an ultrasonic distance sensor). It can be understood that, the feasible way of acquiring the distance is not limited to using a distance sensor, and can be other ways, for example, acquiring the distance between the user and the first infrared thermometer that is directly inputted by the user. In this case, the device using the method for measuring body temperature of the present embodiment has a user interaction function, and the distance between the user and the first infrared thermometer in the device that is inputted by the user is received based on the user interaction function. As another example, the distance between the first infrared thermometer and the photographed object (that is, the user) is acquired by photographing the image and processing the image.

In determining the part to be measured of the user in Step S102, the part to be measured may be the user's ear, nose, forehead etc., which is not limited in the present disclosure.

The method for measuring body temperature of the present disclosure may be applied to various products, such as smart loudspeakers, smart TV sets and service robots, which is not limited in the present disclosure. It will be described in detail by taking the example of a service robot below.

When the service robot is communicating with the user, the user will feel uncomfortable if the distance between them is too small, which cannot meet the demands in practical applications. On the other hand, when the distance between them is too large, because the transmission of infrared energy is easily affected by temperature, humidity and dust particles and so on in the peripheral environment, the larger the distance is, the larger the error is, and the more inaccurate the measurement result is. In addition, because the measurement at a part on the forehead is relatively simple and the forehead is generally flat, the radiated infrared energy is relatively uniform, the measurement error is small, and the measurement data are more accurate. Therefore, as a preferable embodiment of the present disclosure, the part to be measured of the user is the forehead, and the focal length of the Fresnel lens is selected to be 50 cm.

As an example, the case that the method for measuring body temperature is applied to a service robot and the part to be measured of the user is the forehead of the user will be described in detail.

Figure 2:
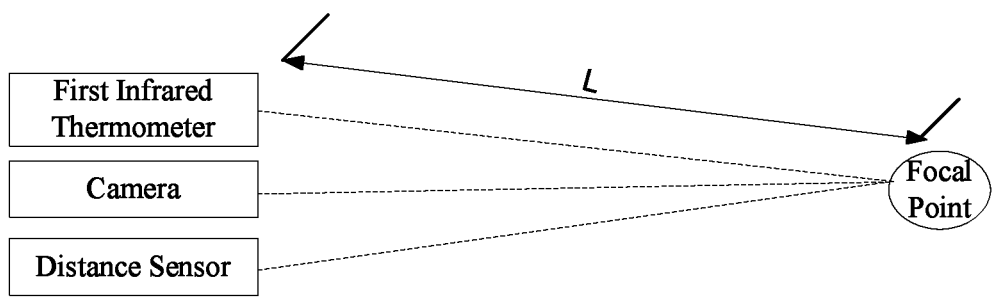
FIG. 2 is a schematic diagram of the positions of related hardware for measuring body temperature according to an embodiment of the present disclosure.

Referring to FIG. 2, on the service robot, a first infrared thermometer, a camera and a distance sensor are provided and placed together, and it is ensured that the center lines of the three converge at the focal point of the Fresnel lens of the first infrared thermometer. For example, the center lines of the three converge at the corresponding position where the focal length L of the Fresnel lens is equal to 50 cm.

It should be noted that, FIG. 2, as a preferable mode, shows the structure in which the first infrared thermometer is at the top, the camera is in the middle and the distance sensor is at the bottom. It is a feasible way in the present disclosure that the first infrared thermometer, the camera and the distance sensor are placed together and it is ensured that the center lines of the three converge at the focal point of the Fresnel lens of the first infrared thermometer. By such a design, the first infrared thermometer can measure the temperature value of a measuring point on the forehead of the user at the distance indicated by the focal length of the Fresnel lens, and the error of the temperature value of the measuring point is smaller than that of the temperature value of a measuring area, so the measurement result is more accurate; that is, the measurement accuracy is improved.

In practical applications, if the requirement on the measurement accuracy is relatively low, the positions of the first infrared thermometer, the camera and the distance sensor may be relatively randomly designed, provided that the respective center lines of the three converge at the focal point of the Fresnel lens of the first infrared thermometer. In addition, in the present disclosure, the placing order of the three is not strictly limited; that is, the placing order of the three in FIG. 2 may be varied. For example, in other embodiments of the present disclosure, optionally, the camera is placed at the top, the first infrared thermometer is placed in the middle, and the distance sensor is placed at the bottom, and it is ensured that the respective center lines of the three converge at the focal point of the Fresnel lens of the first infrared thermometer. Optionally, the camera is placed at the bottom, the distance sensor is placed in the middle, and the first infrared thermometer is placed at the top.

In other words, in practical applications, the positions of the three may be adjusted according to the demand, and is not limited to the present embodiment. Particularly, the adjusting ways may be adjusting the placing order of the three, and may also be adjusting the placing angle of a certain component of the three without adjusting the placing order, for example, adjusting the placing angle of the camera to converge the center line of the camera at the focal point of the Fresnel lens of the first infrared thermometer.

Figure 3:
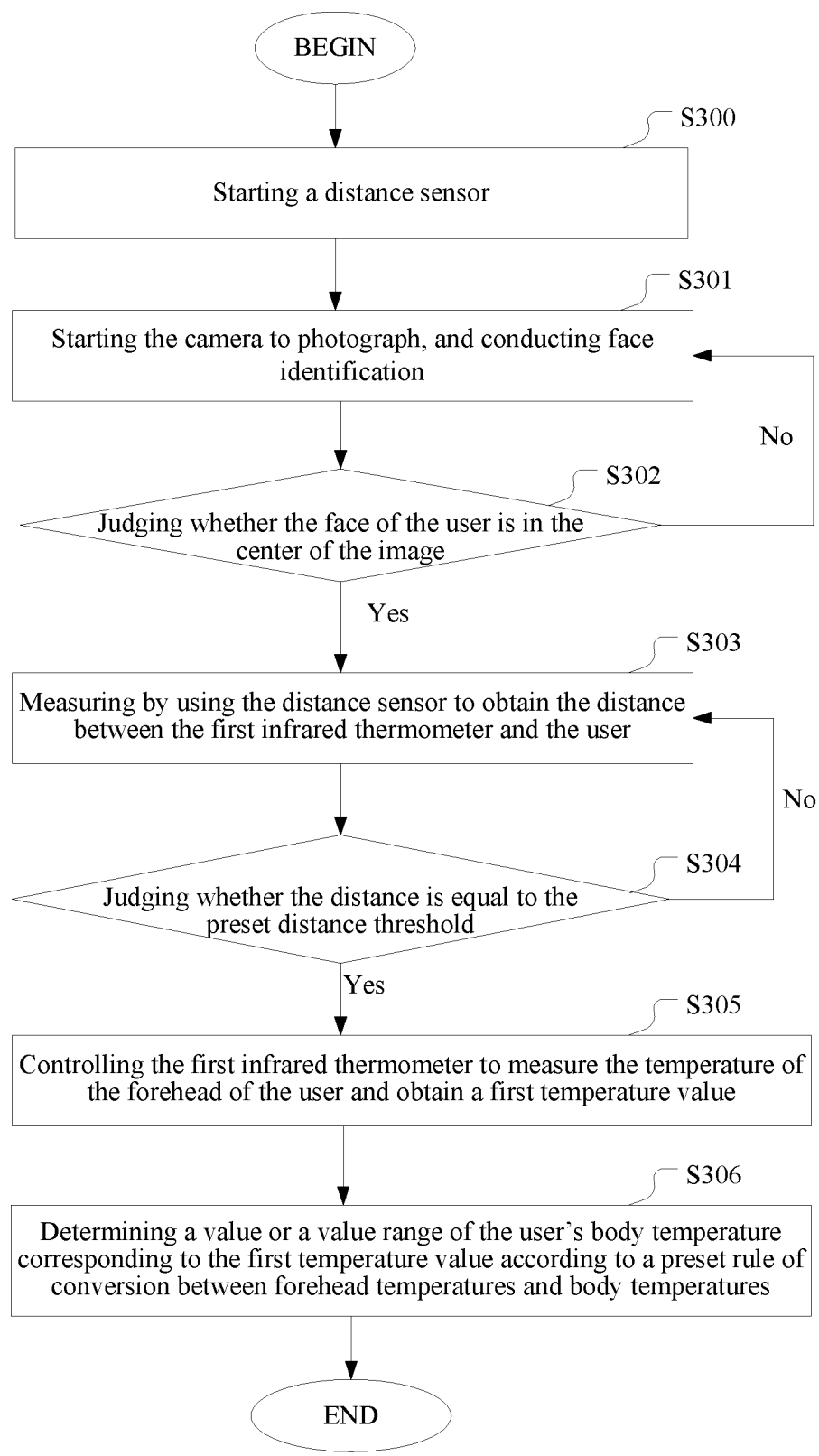
FIG. 3 is a flow chart of a method for measuring body temperature according to an embodiment of the present disclosure.

Referring to FIG. 3, when a temperature measuring instruction is received, the method for measuring body temperature of the present embodiment comprises the following particular steps.

The flow begins.

Step S300, starting a distance sensor.

In order to realize the measurement of the body temperature of the user, in the present embodiment, the distance between the user and the service robot must be acquired. Therefore, in applications, the distance sensor on the service robot may be started before executing Step S301.

Step S301, starting the camera to photograph, and conducting face identification.

The camera is started, and collects the image of the object in front of the service robot to find the target object (that is, the user) whose body temperature is to be measured.

Step S302, judging whether the face of the user is in the center of the image; and if yes, determining that the part to be measured of the user is a part on the forehead, and executing Step S303, and if no, returning to Step S301.

The reason for judging whether the face of the user is in the center of the image in this step is to determine that the user is currently staring at the service robot, and identify out the face region of the user from the image and further determine the part to be measured, i.e., the forehead. When the face of the user is not in the center of the image, it usually indicates that the user is currently not staring at the camera on the service robot but is looking at another object. At this point, the temperature measurement of the user should not be conducted.

A microprocessor on the service robot conducts face identification on the image collected by the camera. For example, by using the pixel coordinate information corresponding to the user face region in the image, judges whether the user is closely facing the camera, that is, judging whether the face of the user is in the center of the image, and if yes, determines a part on the forehead and ensures that the first infrared thermometer aligns with the forehead of the user. It should be noted that, conducting face identification on the image by the microprocessor may be implemented by any feasible way in the prior art, which is not limited herein, provided that the human face region of the user can be identified out according to the image of the user collected by the camera.

Step S303, measuring the distance between the first infrared thermometer and the user by the distance sensor.

In this step, the distance between the user and the first infrared thermometer is measured by the distance sensor, such as an ultrasonic distance sensor. It should be noted that, as the first infrared thermometer is provided in the service robot, when distance measurement is conducted, the distance between the service robot and the user is measured which is equal to the distance between the user and the first infrared thermometer. In other embodiments, the distance may be acquired by other feasible ways, such as the above mentioned way of directly inputting the distance by the user, or a way of obtaining the distance by photographing and processing the image, which is not limited herein.

Step S304, judging whether the distance is equal to the preset distance threshold, and if yes, executing Step S305, and if no, returning to Step S303.

In this step, the present disclosure judges whether the distance between the first infrared thermometer and the user acquired in Step S303 is equal to the preset distance threshold, and when the distance obtained is equal to the preset distance threshold, e.g., 50 cm (an error of 1 cm is allowed), instructs the first infrared thermometer to measure the temperature of the forehead of the user.

In practical applications, when the obtained distance between the first infrared thermometer and the user is not equal to the preset distance threshold, the service robot is controlled to move to a corresponding position, or is controlled to output prompting information to the user, to prompt the user to move to a corresponding position. For example, when the obtained distance between the first infrared thermometer and the user is greater than the preset distance threshold (for example, 50 cm), the service robot may be controlled to move or the user is prompted to move to reduce the distance between the service robot and the user.

Considering the application scenarios of the method for measuring body temperature of the present embodiment, and the fact that the distance between the first infrared thermometer and the user may probably be greater than the preset distance threshold, the present disclosure provides the above two different ways of reducing the distance to satisfy the demands in different scenarios. Particularly, when applied to movable devices such as service robots, the present disclosure may reduce the distance between the service robot and the user by controlling the service robot to move while the user remains stationary, and may also quickly reduce the distance between them by controlling the service robot to move and simultaneously prompting the user to move. However, regarding products that cannot conveniently move in use, such as smart TV sets, the present embodiment can reduce the distance between them by controlling to output a prompting information to the user to prompt the user to move to a corresponding position.

After controlling the service robot and/or the user to move, the present embodiment records the measurement result of the first infrared thermometer when the measurement distance is 50 cm. That is, the present embodiment first controls the service robot and/or the user to move, and only after the service robot and/or the user has moved to a designated position (a position corresponding to the measurement distance 50 cm), controls the first infrared thermometer to measure and obtain a temperature value.

In addition, in other embodiments, after conducting face identification to determine that the camera aligns with the forehead of the user, the present disclosure may control the first infrared thermometer to measure the temperature of the forehead of the user in real time and obtain a plurality of temperature values. In this process, the distance sensor is controlled to measure the distance between the user and the service robot in real time, thereby merely reserving the corresponding temperature value when the distance between the user and the service robot is 50 cm (or an error within plus or minus 1 cm). That is, the present disclosure controls the first infrared thermometer to measure and obtain a plurality of temperature values, and merely uses the corresponding temperature value when the distance between them is 50 cm (or an error within plus or minus 1 cm).

Step S305, controlling the first infrared thermometer to measure the temperature of the forehead of the user and obtain a first temperature value.

The working principle of the first infrared thermometer is that all objects whose temperature is above absolute zero will radiate infrared rays due to the molecular movement of itself. The higher the temperature of the objects is, the more intense the infrared ray radiated is. Temperatures of different parts on human body may be measured by using the infrared rays of particular wave bands emitted by different parts on human body. In this step, the present disclosure controls the first infrared thermometer to measure the temperature of the forehead of the user, and obtain the temperature value of the forehead of the user, that is, the first temperature value.

Step S306, determining a value or a value range of the user's body temperature corresponding to the first temperature value according to the preset rule of conversion between forehead temperatures and body temperatures.

In this step, the present disclosure, after obtaining the first temperature value, conducts conversion according to the preset rule, for example, the following Table 1, that is, accurately converts the measured temperature value of the part on the forehead of the user into a body temperature value.

Herein, the preset rule is a rule of conversion between forehead temperatures and body temperatures, for example, in practical applications, it may be a forehead temperature and body temperature conversion table (that is, Table 1). Table 1 records forehead temperatures and the corresponding values or value ranges of the user's body temperature. Schematically, Table 1 records that the forehead temperature of 33.2 degree Celsius corresponds to a user's body temperature value of 35.5 degree Celsius, the forehead temperature of 33.4 degree Celsius corresponds to a user's body temperature value of 35.7 degree Celsius, and the forehead temperature of 35 degree Celsius corresponds to a user's body temperature value of 37 degree Celsius.

It should be noted that, the case that one forehead temperature value is corresponding to one body temperature value is described here, but in other embodiments, one forehead temperature value may correspond to one body temperature value range. For example, the forehead temperature of 33.2 degree Celsius corresponds to a body temperature value range of the user of 35.1 degree Celsius to 35.9 degree Celsius, which is not limited herein.

TABLE 1

| forehead temperature | body temperature |
| --- | --- |
| 33.2 | 35.5 |
| 33.4 | 35.7 |
| 33.6 | 35.9 |
| 33.8 | 36 |
| 34 | 36.1 |
| 34.2 | 36.4 |
| 34.4 | 36.5 |
| 34.6 | 36.7 |
| 34.8 | 36.9 |
| 35 | 37 |
| 35.2 | 37.2 |
| 35.4 | 37.3 |
| 35.6 | 37.5 |
| 35.8 | 37.7 |
| 36 | 37.8 |
| 36.2 | 38 |
| 36.4 | 38.1 |
| 36.6 | 38.2 |
| 36.8 | 38.4 |
| 37 | 38.5 |

TABLE 1-continued

| forehead temperature | body temperature |
|---|---|
| 37.2 | 38.7 |
| 37.4 | 38.8 |
| 37.6 | 38.9 |
| 37.8 | 39.1 |
| 38 | 39.2 |
| 38.2 | 39.3 |
| 38.4 | 39.5 |
| 38.6 | 39.6 |
| 38.8 | 39.7 |
| 39 | 39.8 |

Table 1 is a comparison table of forehead temperatures and human body temperatures. After a first body temperature value, that is, a forehead temperature, is obtained, by looking up the conversion table of forehead temperatures and human body temperatures, the corresponding body temperature of the user can be determined. Till now, the flow ends.

Considering that in practical applications environmental and other factors will interfere and affect the body temperature measurement result, in another embodiment, in order to reduce the influence of humidity, temperature and dust particles in the measurement environment on the temperature measurement result, and improve the measurement accuracy, the present disclosure proposes a solution of providing a reference object whose temperature is known and constant, and comprehensively determining the user's body temperature by using the measured temperatures of the reference object and the forehead of the user, to reduce the measurement error and improve the measurement accuracy.

Here, the structure of the reference object, the environment where the reference object is located and the distance of the reference object are described first.

Continuing with the above embodiment, the reference object of the present embodiment is provided on the service robot, and comprises a skin-like surface (the skin-like surface is similar to human body skin, which can reduce the measurement error), a heater and a temperature feedback control circuit. The temperature of the skin-like surface of the reference object is constant; for example, the temperature is set to be the normal temperature of the human body forehead, that is, 35 degree Celsius. The heater and the temperature feedback control circuit are provided in the skin-like surface of the reference object. As a heat source, the heater can generate thermal energy. The function of the temperature feedback control circuit is to measure the current temperature of the reference object, and if the current temperature of the reference object exceeds a preset temperature value (for example, 35 degree Celsius), control the heater to stop heating, and wait for temperature falling; and when the temperature of the reference object falls to below 35 degree Celsius, control the heater to heat, thereby maintaining the temperature value of the reference object at the preset temperature value.

In addition, in order to accurately determine the degree of the influence of environmental factors on the body temperature measurement, and then eliminate the influences and reduce the measurement error, the present embodiment simulates and establishes the environment where the reference object is located according to the environment where the user is located. Particularly, the present disclosure designs a reasonable ventilation structure at the position in the service robot corresponding to the reference object, to make the internal environment of the service robot where the reference object is located and the external environment of the service robot where the user is located to maintain the same. For example, a ventilation opening is provided at the position of the service robot corresponding to the reference object, and accordingly, air in the environment where the user is located (for example, indoors) enters the service robot, so that the environment where the reference object is located and the environment where the user is located are the same. If only one ventilation opening is provided, the sphere of air flow and its influence are limited, so an air duct (air passage) may be provided, that is, an air inlet and a ventilation opening may be provided to ensure the circulation and convection of air. In addition, a shielding box may be provided at an vacant position of the service robot that is far away from the circuit board and other heat sources, and the reference object is place in the shielding box, to prevent the thermal energy emitted from inside the service robot in the working process of the service robot from affecting the temperature of the reference object, and thus improve the accuracy of the body temperature measurement of the user.

In the present embodiment, the reference object individually corresponds to an infrared thermometer, i.e., a second infrared thermometer, and the temperature of the reference object is measured by the second infrared thermometer.

Considering that the measurement distance also affects the measured temperature of the reference object, in the present embodiment, the reference object is placed at a position from which the distance to the second infrared thermometer is a preset distance threshold. The preset distance threshold is set according to the focal length of the Fresnel lens of the first infrared thermometer. Such a design can ensure that the two infrared thermometers measure the temperature of the user or the temperature of the reference object at the same distance, thereby preventing the error of the measurement result caused by different distances.

After providing the reference object, the method for measuring body temperature of the present embodiment in which the measured temperature of the reference object is used to reduce the measurement error is described.

Figure 4:
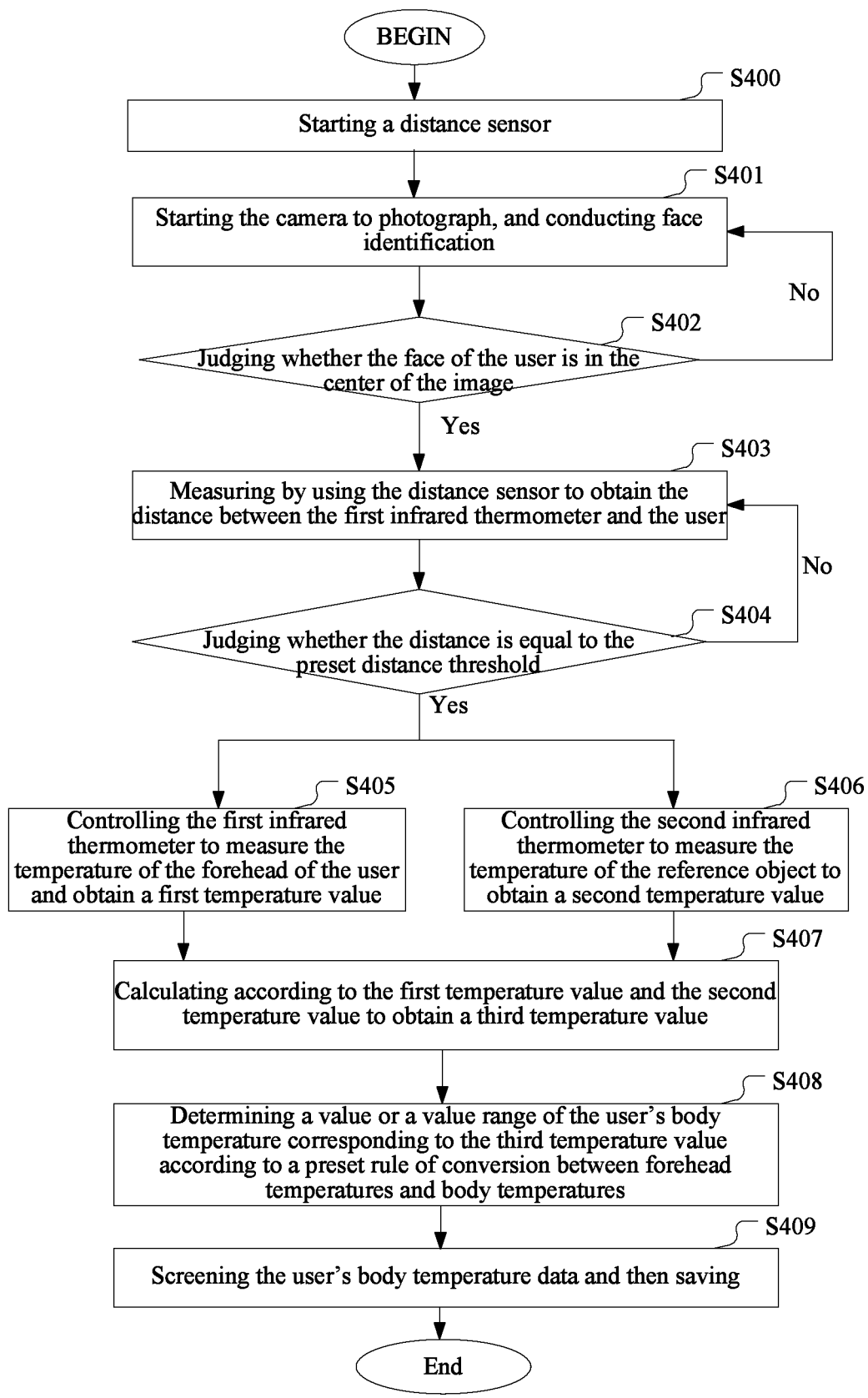
FIG. 4 is a flow chart of a method for measuring body temperature according to an embodiment of the present disclosure.

Referring to FIG. 4, the method for measuring body temperature of the present embodiment comprises the following steps.

The flow begins.

Step S400, starting a distance sensor.

In order to facilitate subsequently acquiring the distance between the user and the service robot, when implementing the method, the present disclosure may start the distance sensor on the service robot first and then execute Step S401.

Step S401, starting the camera to photograph, and conducting face identification.

Step S402, judging whether the face of the user is in the center of the image; and if yes, determining that the part to be measured of the user is a part on the forehead, and executing Step S403, and if no, returning to Step S401.

Step S403, measuring and obtaining the distance between the first infrared thermometer and the user by the distance sensor.

Step S404, judging whether the distance is equal to the preset distance threshold, and if yes, executing Step S405 and Step S406, and if no, returning to Step S403.

Step S405, controlling the first infrared thermometer to measure the temperature of the forehead of the user, and obtain a first temperature value.

It should be noted that, Step S401 to Step S405 of the present embodiment are the same as Step S301 to Step S305 in FIG. 3 of the above embodiment, so the details of Step S401 to Step S405 in the present embodiment may refer to the corresponding steps of FIG. 3 and will not be further described here.

The present embodiment differs from the embodiment corresponding to FIG. 3 in Step S406 to Step S409, which will be emphatically described below.

Step S406, controlling the second infrared thermometer to measure the temperature of the reference object and obtain a second temperature value.

In this step, the present disclosure measures the temperature of the reference object in the service robot by the second infrared thermometer and obtains a second temperature value. Although the temperature of the reference object is known and constant, in the actual measurement, due to the influence of the environment, there must be a difference between the temperature value measured by the second infrared thermometer and the actual temperature of the reference object, and the difference reflects the degree of the influence of the measurement environment on the body temperature measurement result.

Step S407, calculating according to the first temperature value and the second temperature value to obtain a third temperature value.

On the basis of obtaining the first temperature value and the second temperature value respectively by Step S405 and Step S406, the present disclosure calculates according to the first temperature value and the second temperature value to obtain a third temperature value. Particularly, the calculating formula is as follows:

$$C = \frac{A+273}{B+273} \times (e+273) - 273$$

wherein, C is the third temperature value, A is the first temperature value, B is the second temperature value, and e is the constant temperature value of the reference object (for example, 35 degree Celsius).

Here, in order to avoid expressing temperatures using negative numbers and 0, all of the calculations of the temperature values are conducted on the basis that the thermodynamic temperatures of an object is standardized and quantized. For example, if the temperature values of two objects are multiplied, and they are expressed by degree Celsius, when the temperature value of one of the objects is 0 degree Celsius, the multiplication result of them will be 0 degree Celsius. However, in fact, after the numerical values of two indicated temperatures are multiplied, it should be larger than the numerical value of one of the indicated temperatures, that is, higher than the temperature value of one of the objects. It can be seen that, if the temperature value is expressed by degree Celsius, the calculating is impossible. Therefore, the present embodiment converts both of the first temperature value and the second temperature value obtained into absolute temperatures first and then calculates to obtain the third temperature value.

Step S408, determining a value or a value range of the user's body temperature corresponding to the third temperature value according to a preset rule of conversion between forehead temperatures and body temperatures.

In this step, after obtaining the third temperature value, similarly to the above Step S306, by looking up the above Table 1 according to a preset rule of conversion between forehead temperatures and body temperatures, a value or a value range of the user's body temperature corresponding to the third temperature value can be determined.

Step S409, screening and then saving the user's body temperature data.

This step screens the user's body temperature data, eliminates unreasonable data, and sends the screened body temperature data to a human body health application in the service robot to be used. Here the unreasonable data comprise body temperature data that exceed a preset range (for example, 35 degree Celsius to 40 degree Celsius). For example, when the forehead of the user is exposed, the forehead temperature measured is 34.6 degree Celsius, and according to the rule of conversion between forehead temperatures and body temperatures, the corresponding body temperature is 36.7 degree Celsius, so this datum may be reserved. However, when the forehead of the user is shielded (for example, by the hair of the user), the forehead temperature measured is about 31 degree Celsius, and according to the rule of conversion between forehead temperatures and body temperatures, the corresponding body temperature datum is about 34 degree Celsius which exceeds the temperature range of 35 degree Celsius to 40 degree Celsius, so it is an unreasonable datum. In addition, in some extreme conditions, for example, when the room temperature is minus 10 degree Celsius or exceeds 40 degree Celsius, the measurement result of the forehead temperature will be extraordinarily abnormal, for example, above 40 degree Celsius, and these unreasonable data must be screened out.

Till now, the flow ends.

It should be noted that, in the above embodiments shown in FIG. 3 and FIG. 4, the distance sensor is started first, then the camera is started to photograph the user, and then the distance between the first infrared thermometer and the user is acquired by the distance sensor, but the present disclosure are not limited thereto. For example, the present disclosure may start the camera first to photograph the user, determine the part to be measured of the user according to the image, then start the distance sensor, acquire the distance between the first infrared thermometer and the user by the distance sensor, and when the distance between them is equal to the preset distance threshold, control the infrared temperature measurement. In practical applications, the process may be set and selected according to demands.

Figure 5:
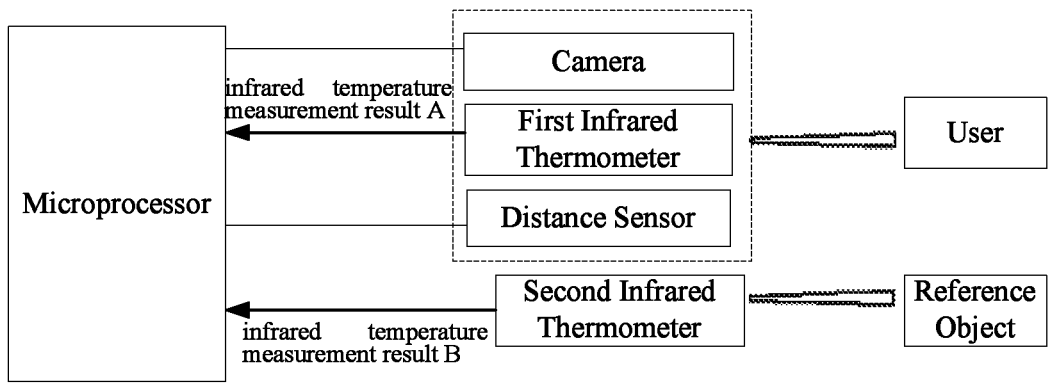
FIG. 5 is a schematic diagram of the body temperature measuring according to an embodiment of the present disclosure.

FIG. 5 is a schematic diagram of the body temperature measuring according to an embodiment of the present disclosure. Referring to FIG. 5, the measurement result A of the forehead temperature of the user measured by the cooperation of the camera, the first infrared thermometer and the distance sensor, that is, the first temperature value, is inputted to the microprocessor, and the measurement result B of the temperature of the reference object measured by the second infrared thermometer, that is, the second temperature value, is also inputted to the microprocessor. The microprocessor calculates and obtains a third temperature value according to the first temperature value and the second temperature value, and according to a preset rule of conversion between forehead temperatures and body temperatures, determines a value or a value range of the user's body temperature corresponding to the third temperature value.

Figure 6:
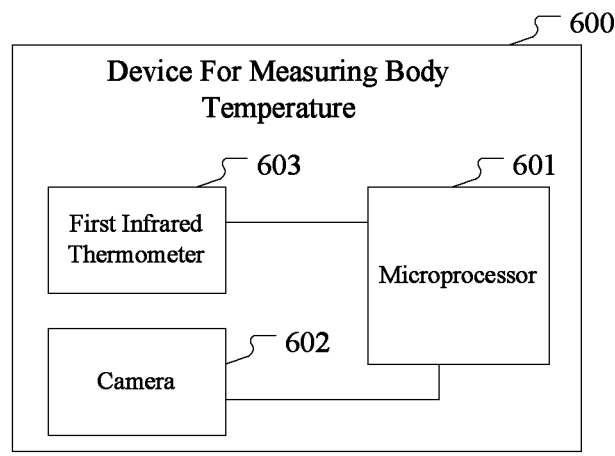
FIG. 6 is a structural block diagram of a device for measuring body temperature according to an embodiment of the present disclosure.

Correspondingly to the above method for measuring body temperature, the present embodiment provides a device for measuring body temperature. Referring to FIG. 6, the device for measuring body temperature 600 comprises: a main body, a microprocessor 601 provided on the main body, and a camera 602 and a first infrared thermometer 603 that are connected to the microprocessor 601.

The microprocessor 601, when a temperature measuring instruction is received, starts the camera 602 and the first infrared thermometer 603.

After being started, the camera 602 photographs a user to obtain an image, and sends the image to the microprocessor 601.

The microprocessor 601 determines a part to be measured of the user according to the received image, and according to an acquired distance between the first infrared thermometer 603 and the user, when it is determined that the distance is equal to a preset distance threshold, controls the first infrared thermometer 603 to measure the temperature of the part to be measured of the user, and processes the temperature, to obtain a value or a value range of the user's body temperature.

The preset distance threshold is set according to a focal length of a Fresnel lens of the first infrared thermometer 603.

In an embodiment, the device for measuring body temperature 600 further comprises a distance sensor, and the distance sensor is connected to the microprocessor 601.

The distance sensor, the first infrared thermometer 603 and the camera 602 are all provided on the main body, and the positions of the three satisfy a condition that the respective center lines of them converge at the focal point of the Fresnel lens of the first infrared thermometer 603.

After being started, the distance sensor measures the distance between the first infrared thermometer 603 and the user, and sends the measured distance information to the microprocessor 601.

The microprocessor 601 conducts face identification on the received image, and controls the first infrared thermometer 603 to measure the temperature of the part to be measured of the user and obtain a first temperature value, when identifying out that a human face region is located in a central position of the image and determining that the distance is equal to the preset distance threshold. Here, the part to be measured of the user may be a part on the forehead of the user.

In an embodiment of the present disclosure, the device for measuring body temperature 600 further comprises a reference object provided on the main body. The reference object comprises a skin-like surface, a heater and a temperature feedback control circuit.

The temperature feedback control circuit of the reference object is connected to the heater, the temperature feedback control circuit collects a current temperature value of the reference object, and controls the heater according to the collected current temperature value, to maintain a temperature value of the reference object at a constant temperature value.

The main body is provided with a ventilation opening and an air duct at a position corresponding to the reference object.

The main body is provided with a second infrared thermometer at a position from which the distance to the reference object is constant and is equal to the preset distance threshold.

The second infrared thermometer is connected to the microprocessor 601, and the second infrared thermometer measures a temperature of the reference object under the control of the microprocessor 601 and obtains a second temperature value.

The microprocessor 601 is particularly for, according to a preset rule, the first temperature value and the second temperature value, determining a value or a value range of the user's body temperature.

For example, the microprocessor 601 calculates and obtains a third temperature value according to the first temperature value and the second temperature value, and according to a preset rule of conversion between forehead temperatures and body temperatures, determines a value or a value range of the user's body temperature corresponding to the third temperature value and saves it in a memory; and screens values or value ranges of the user's body temperature in the memory, and selects a value or a value range of the user's body temperature within a preset temperature value range.

In an embodiment, the main body is a service robot, and the distance sensor, the first infrared thermometer 603 and the camera 602 are provided at the head of the service robot.

The device for measuring body temperature 600 further comprises a driving module (for example, an electrical motor) connected to the microprocessor 601, and the microprocessor 601 is further for, when determining that the obtained distance between the first infrared thermometer 603 and the user is not equal to the preset distance threshold, controlling the driving module to drive the service robot to move to a corresponding position;

and/or, the device for measuring body temperature 600 further comprises a prompting module connected to the microprocessor 601, and the microprocessor 601, when determining that the obtained distance between the first infrared thermometer 603 and the user is not equal to the preset distance threshold, controls the prompting module to output a prompting information to the user, to prompt the user to move to a corresponding position.

In other words, in an embodiment of the present disclosure, only the driving module is provided, and the driving module is controlled to drive the service robot to move to change the distance between the first infrared thermometer and the user. For example, the distance between the first infrared thermometer and the user is currently 80 cm, and the preset distance threshold is 50 cm. It can be judged that they are not equal, so the microprocessor in the service robot controls the driving module (for example, an electrical motor) to rotate, the electrical motor rotates to drive the wheels of the service robot to move so that the service robot moves to a position from which the distance to the user is 50 cm, and the microprocessor controls the electrical motor to stop rotating. Optionally, in an embodiment of the present disclosure, a prompting module is provided, and when the microprocessor determines that the distance between the first infrared thermometer and the user is not equal to the preset distance threshold, the microprocessor controls the prompting module (for example, an audio outputting module) to output voice prompting information, which may be "will you please move forwardly by 20 cm", to prompt the user to move to a corresponding position. Optionally, in an embodiment of the present disclosure, the driving module and the prompting module are both provided to control the device and/or the user to move so that the distance between the first infrared thermometer and the user is equal to the preset distance threshold, thereby improving the measurement accuracy.

It should be noted that, the device for measuring body temperature of the present embodiment is corresponding to the method for measuring body temperature of the above embodiment, so the working process of the device for measuring body temperature of the present embodiment may refer to the above embodiment, and is not further described here.

Figure 7:
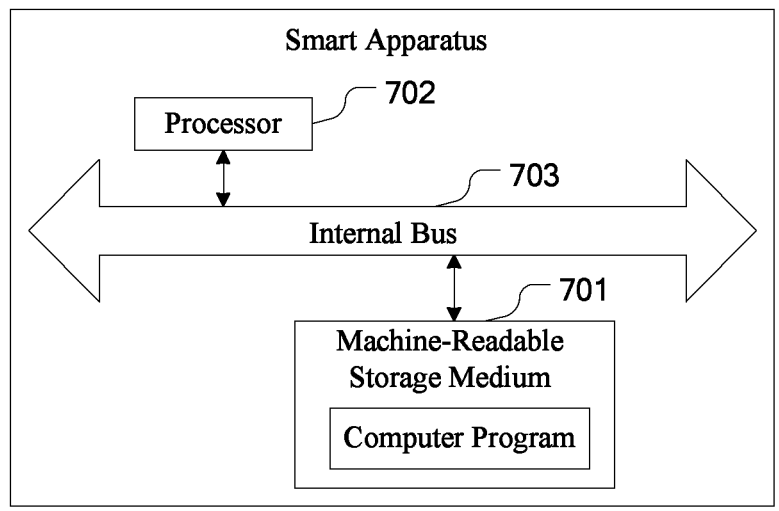
FIG. 7 is a structural block diagram of a smart apparatus according to an embodiment of the present disclosure.

On the basis of the same inventive concept of the above embodiment, the present disclosure provides a smart apparatus as shown in FIG. 7. FIG. 7 is a structural block diagram of a smart apparatus according to an embodiment of the present disclosure. The smart apparatus comprises a machine-readable storage medium 701 and a processor 702 that are communicatively connected by an internal bus 703, the machine-readable storage medium 701 stores a computer program executable by the processor 702, and when executed by the processor 702 the computer program implements the steps of the method for measuring body temperature of the present disclosure.

In different embodiments, the machine-readable storage medium 701 may be a random access memory or a nonvolatile memory. The nonvolatile memory may be a storage drive (such as hard disk drive), a solid state disk, any type of memory discs (such as optical disc and DVD), or similar storage media, or a combination thereof. The random access memory may be an RAM (Random Access Memory), a volatile memory, a nonvolatile memory and a flash memory. Further, the nonvolatile memory and the random access memory, as the machine-readable storage medium, can store the computer program executed by the processor 702.

In conclusion, with respect to the problem in the prior art that the body temperature measurement cannot satisfy the accuracy requirement of long-distance temperature measurement, the method and device for measuring body temperature and the smart apparatus of the present disclosure, measures the temperature of the part to be measured of the user by controlling the measurement distance and reducing the temperature measurement error caused by factors such as environment, and convert the temperature of the part to be measured into a value or a value range of the user's body temperature according to a preset rule, thereby satisfying the requirement of long-distance body temperature measurement while ensuring the accuracy of the body temperature measurement.

The above merely describes particular embodiments of the present disclosure. By the teaching of the present disclosure, a person skilled in the art can make other modifications or variations on the basis of the above embodiments. A person skilled in the art should appreciate that, the above detailed description is only for the purpose of better explaining the present disclosure, and the protection scope of the present disclosure should be subject to the protection scope of the claims.

What is claimed is:

1. A method for measuring body temperature, comprising:
    starting a camera and a first infrared thermometer when a temperature measuring instruction is received;
    photographing a user by using the camera to obtain an image, and identifying the image to determine a part to be measured of the user;
    acquiring a distance between the first infrared thermometer and the user;
    controlling the first infrared thermometer to measure a temperature of the part to be measured of the user and obtain a first temperature value when the distance is equal to a preset distance threshold, wherein the preset distance threshold is set according to a focal length of a Fresnel lens of the first infrared thermometer;
    determining a value or a value range of a user's body temperature according to a preset rule and the measured temperature;
    providing a reference object and simulating an external environment to construct an environment of the reference object, wherein the reference object comprises a skin-like surface, a heater and a temperature feedback control circuit, and a temperature value of the reference object is constant;
    providing a second infrared thermometer for measuring a temperature of the reference object, wherein a distance between the second infrared thermometer and the reference object is constant and is equal to the preset distance threshold;
    controlling the second infrared thermometer to measure the temperature of the reference object and obtain a second temperature value; and
    determining the value or the value range of the user's body temperature according to the preset rule and the first temperature value and the second temperature value obtained.

2. The method according to claim 1, further comprising:
    starting a distance sensor, and measuring by using the distance sensor to obtain the distance between the first infrared thermometer and the user when the temperature measuring instruction is received;
    wherein the identifying the image comprises conducting face identification on the image, and
    controlling the first infrared thermometer to measure the temperature of the part to be measured of the user to obtain the first temperature value when it is identified out that a human face region is located in a central position of the image and the distance is equal to the preset distance threshold.

3. The method according to claim 2, wherein the method is applied to a service robot, and
    the method further comprises: controlling the service robot to move to a corresponding position when the obtained distance between the first infrared thermometer and the user is not equal to the preset distance threshold.

4. The method according to claim 2, wherein the method is applied to a service robot, and
    the method further comprises: controlling to output prompting information to the user to prompt the user to move to a corresponding position when the obtained distance between the first infrared thermometer and the user is not equal to the preset distance threshold.

5. The method according to claim 1, wherein a step of identifying the image to determine a part to be measured of the user comprises:
    conducting face identification on the image, to determine a part on a user's forehead as the part to be measured, and
    calculating according to the first temperature value and the second temperature value to obtain a third temperature value, and determining the value or the value range of the user's body temperature corresponding to the third temperature value according to a preset rule of conversion between forehead temperatures and body temperatures.

6. The method according to claim 1, further comprising:
    screening values or value ranges of the user's body temperature that have been determined, and selecting and saving a value or a value range of the user's body temperature within a preset temperature value range.

7. A device for measuring body temperature, comprising: a main body, a microprocessor provided on the main body, and a camera and a first infrared thermometer that are connected to the microprocessor;
    wherein when a temperature measuring instruction is received, the microprocessor starts the camera and the first infrared thermometer;
    after being started, the camera, photographs a user to obtain an image, and sends the image to the microprocessor; and
    the microprocessor determines a part to be measured of the user according to the received image, and according to an acquired distance between the first infrared thermometer and the user, when it is determined that the distance is equal to a preset distance threshold, controls the first infrared thermometer to measure a temperature of the part to be measured of the user and obtain a first temperature value, and processes the temperature to obtain a value or a value range of a user's body temperature;

wherein the preset distance threshold is set according to a focal length of a Fresnel lens of the first infrared thermometer;

wherein the device further comprises a reference object provided on the main body, the reference object comprises a skin-like surface, a heater and a temperature feedback control circuit, the temperature feedback control circuit of the reference object is connected to the heater, the temperature feedback control circuit collects a current temperature value of the reference object, and controls the heater according to the collected current temperature value, to maintain a temperature value of the reference object at a constant temperature value;

the main body is provided with a ventilation opening and an air duct at a position corresponding to the reference object, the main body is provided with a second infrared thermometer at a position from which the distance to the reference object is constant and is equal to the preset distance threshold, and the second infrared thermometer is connected to the microprocessor, the second infrared thermometer measures a temperature of the reference object under the control of the microprocessor and obtains a second temperature value, and the microprocessor is particularly for, according to a preset rule, the first temperature value and the second temperature value, determining the value or the value range of the user's body temperature.

8. The device according to claim 7, further comprising a distance sensor connected to the microprocessor;

the distance sensor, the first infrared thermometer and the camera are all provided on the main body, and the positions of the distance sensor, the first infrared thermometer and the camera satisfy a condition that respective center lines of the distance sensor, the first infrared thermometer and the camera converge at a focal point of the Fresnel lens of the first infrared thermometer;

after being started, the distance sensor, measures the distance between the first infrared thermometer and the user, and sends the measured distance information to the microprocessor, and the microprocessor conducts face identification on the received image, and controls the first infrared thermometer to measure the temperature of the part to be measured of the user and obtain the first temperature value, when identifying out that a human face region is located in a central position of the image and determining that the distance is equal to the preset distance threshold.

9. The device according to claim 7, wherein the part to be measured of the user is a part on a user's forehead, the microprocessor calculates according to the first temperature value and the second temperature value to obtain a third temperature value, and according to a preset rule of conversion between forehead temperatures and body temperatures, determines the value or the value range of the user's body temperature corresponding to the third temperature value and saves it in a memory.

10. The device according to claim 9, wherein the main body is a service robot, and the microprocessor screens values or value ranges of the user's body temperature in the memory, and selects a value or a value range of the user's body temperature within a preset temperature value range to be used by a human body health application in the service robot.

11. The device according to claim 7, wherein the main body is a service robot, and the device further comprises:

a driving module connected to the microprocessor, and the microprocessor is further for, when determining that the obtained distance between the first infrared thermometer and the user is not equal to the preset distance threshold, controlling the driving module to drive the service robot to move to a corresponding position.

12. The device according to claim 7, further comprising:

a prompting module connected to the microprocessor, and the microprocessor, when determining that the obtained distance between the first infrared thermometer and the user is not equal to the preset distance threshold, controls the prompting module to output a prompting information to the user to prompt the user to move to a corresponding position.

13. A smart apparatus, comprising a machine-readable storage medium and a processor that are communicatively connected by an internal bus, and a camera, a first infrared thermometer, a second infrared thermometer and a reference object, wherein the machine-readable storage medium stores a computer program executable by the processor, and the camera, the first infrared thermometer and the second infrared thermometer are connected with the processor, the reference object comprises a skin-like surface, a heater and a temperature feedback control circuit, and a temperature value of the reference object is constant, a distance between the second infrared thermometer and the reference object is constant and is equal to a preset distance threshold, and when the computer program is executed by the processor the processor is caused to perform the following operations:

starting the camera and the first infrared thermometer when a temperature measuring instruction is received;

photographing a user by using the camera to obtain an image, and identifying the image to determine a part to be measured of the user;

acquiring a distance between the first infrared thermometer and the user;

controlling the first infrared thermometer to measure a temperature of the part to be measured of the user and obtain a first temperature value when the distance is equal to the preset distance threshold, wherein the preset distance threshold is set according to a focal length of a Fresnel lens of the first infrared thermometer;

controlling the second infrared thermometer to measure the temperature of the reference object and obtain a second temperature value; and determining a value or a value range of a body temperature of the user according to a preset rule and the first temperature value and the second temperature value obtained.

14. The smart apparatus according to claim 13, further comprising a distance sensor, and the distance sensor is connected to the microprocessor, and the processor is further caused to perform the following operations:

starting the distance sensor, and measuring by using the distance sensor to obtain the distance between the first infrared thermometer and the user when the temperature measuring instruction is received;

wherein the identifying the image comprises conducting face identification on the image, and controlling the first infrared thermometer to measure the temperature of the part to be measured of the user to obtain the first temperature value when it is identified out that a human face region is located in a central position of the image and the distance is equal to the preset distance threshold.

15. The smart apparatus according to claim 14, further comprising a service robot as a main body, the service robot controllable by the processor to move to a corresponding position when the obtained distance between the first infrared thermometer and the user is not equal to the preset distance threshold.

16. The smart apparatus according to claim 13, wherein the identifying the image to determine a part to be measured of the user comprises:

conducting face identification on the image, to determine a part on a user's forehead as the part to be measured, and calculating according to the first temperature value and the second temperature value to obtain a third temperature value, and determining the value or the value range of the user's body temperature corresponding to the third temperature value according to a preset rule of conversion between forehead temperatures and body temperatures.

17. The smart apparatus according to claim 14, further comprising a service prompting module connected to the microprocessor, and the processor is further caused to control the prompting module to output prompting information to the user to prompt the user to move to a corresponding position when the obtained distance between the first infrared thermometer and the user is not equal to the preset distance threshold.

* * * * *